United States Patent [19] [11] 4,367,342
Wulff et al. [45] * Jan. 4, 1983

[54] OLEFIN EPOXIDATION

[75] Inventors: Harald P. Wulff, Alameda, Calif.; Freddy Wattimena, Amsterdam, Netherlands

[73] Assignee: Shell Oil Company, Houston, Tex.

[*] Notice: The portion of the term of this patent subsequent to May 3, 1994, has been disclaimed.

[21] Appl. No.: 909,887

[22] Filed: May 26, 1978

Related U.S. Application Data

[63] Continuation of Ser. No. 747,160, Dec. 3, 1976, abandoned, which is a continuation of Ser. No. 173,325, Aug. 19, 1971, abandoned, which is a continuation of Ser. No. 812,920, Apr. 2, 1969, abandoned.

[51] Int. Cl.$^3$ ............................................. C07D 301/19
[52] U.S. Cl. .................................................. 549/529
[58] Field of Search ..................... 260/348.29; 549/529

[56] References Cited

U.S. PATENT DOCUMENTS

| | | | |
|---|---|---|---|
| 3,351,635 | 11/1967 | Kollar | 260/348.29 |
| 3,391,214 | 7/1968 | Fetterly | 260/348.29 |
| 3,505,360 | 4/1970 | Allison et al. | 260/348.29 |
| 4,021,454 | 5/1977 | Wulff et al. | 260/348.29 |

FOREIGN PATENT DOCUMENTS 1524851 4/1968 France.

OTHER PUBLICATIONS

F. Mashio et al., Sci. Technol. (1967) No. 16, pp. 79–85.
S. Kato, Sekiyu to Sekiyu Kagaku (1968), vol. 12(9), pp. 44–49.

*Primary Examiner*—Norma S. Milestone

[57] ABSTRACT

Alkene oxides are produced by the reaction of an organic hydroperoxide and an alkene in the presence of a catalyst of an inorganic oxygen compound of silicon in chemical combination with an oxide or hydroxide of titanium.

19 Claims, No Drawings

OLEFIN EPOXIDATION

This application is a continuation of application Ser. No. 747,160, filed Dec. 3, 1976 which is a continuation of application Ser. No. 173,325 filed Aug. 19, 1971, which is in turn a continuation-in-part of application Ser. No. 812,920 filed Apr. 2, 1969, all now abandoned.

BACKGROUND OF THE INVENTION

The use of organic hydroperoxides in the epoxidation of olefins is known to offer important and distinct advantages over other methods of olefin oxide production. Organic hydroperoxides are relatively inexpensive and convenient and safe to handle. In addition, organic hydroperoxides can readily be obtained and maintained in anhydrous form, thus minimizing potential olefin oxide recovery and purification problems. Also, during the epoxidation reaction, the organic hydroperoxide is converted to other valuable products.

A variety of catalysts has been employed for the reaction of olefins with hydroperoxides. One process is that of Smith, U.S. Pat. No. 2,754,325, issued July 10, 1956, wherein soluble heteropoly acids containing transition metals such as chromium, molybdenum and tungsten are employed as homogeneous catalysts for the reaction of olefins and peroxides such as organic hydroperoxides and hydrogen peroxide. More recently, U.S. Pat. No. 3,350,422 and U.S. Pat. No. 3,351,635, issued Oct. 31, 1967, and Nov. 7, 1967, respectively, to Kollar describe the use of solutions of transition metal compounds (V, Mo, W, Ti, Nb, Ta, Re, Se, Zr, Te and U) as homogeneous catalysts. Although sufficiently soluble compounds of those transition metals generally may be suitable as homogeneous catalysts, their commonly available insoluble compounds, especially inorganic, in general are ineffective as catalysts. For Example, U.S. Pat. No. 3,350,422 discloses that epoxidation of propylene with cumene hydroperoxide employing insoluble vanadium pentoxide as catalyst results in a propylene oxide yield (6%) which is little better than that obtained with no catalyst (4%). Similarly, inorganic compounds, particularly the oxides, of the metals disclosed in U.S. Pat. No. 3,351,635, are generally ineffective as heterogeneous catalysts. For example, as the result of experimentation, it has been found that in the reaction of 1-octene with t-butylhydroperoxide, a commercial $TiO_2$ gave a 50% conversion of hydroperoxide but essentially zero selectivity to 1-octene oxide; $ZrO_2$ gave a 76.7% conversion of hydroperoxide and essentially zero selectivity to 1-octene oxide; $Ta_2O_5$ gave a 11% conversion of hydroperoxide but only a 5% selectivity to 1-octene oxide; $CrO_3$ gave a 99% conversion of hydroperoxide but only a 22% selectivity to 1-octene oxide; $WO_3$ gave an 85% conversion of hydroperoxide but only an 8% selectivity to 1-octene oxide; $Re_2O_7$ gave an essentially quantitative conversion of hydroperoxide but essentially zero selectivity to 1-octene oxide; $TeO_2$ gave a 33% conversion of hydroperoxide but only a 7% selectivity to 1-octene oxide; $SeO_2$ gave a 97% conversion of hydroperoxide but essentially a zero selectivity to 1-octene oxide and $UO_2$ gave a 55% conversion of hydroperoxide but only 5% selectivity to 1-octene oxide. It would be of advantage, however, to effect the epoxidation of olefins with insoluble catalysts in a heterogeneous system, i.e., catalyst compositions which are substantially insoluble in the reaction mixture since heterogeneous catalyst systems generally exhibit a number of operational advantages for large-scale industrial operations. For example, heterogeneous catalyst systems do not require elaborate means for separation of catalyst composition and reaction products due to the insolubility of the catalyst composition in the reaction mixture.

SUMMARY OF THE INVENTION

It has now been found that improved epoxidation of alkenes with hydrocarbon hydroperoxides is effected with a catalyst composition of an inorganic oxygen compound of silicon and an oxide or hydroxide of titanium in chemical combination. The catalyst composition is characterized by being essentially insoluble in the epoxidation reaction mixture providing a heterogeneous system. Moreover, the catalyst composition is further characterized by producing high alkene oxide selectivity based on hydroperoxide converted although the catalyst precursors alone, e.g., $TiO_2$, produce hydroperoxide conversion but give essentially zero selectivity to alkene oxide product.

DESCRIPTION OF PREFERRED EMBODIMENTS

The Catalyst

The catalyst composition employed for the epoxidation comprises an inorganic oxygen compound of silicon in chemical combination with an oxide or hydroxide of titanium. The oxide or hydroxide of titanium is preferably combined with the oxygen compound of silicon in a high positive oxidation state, e.g., tetravalent titanium. The proportion of the oxide or hydroxide of titanium combined in the catalyst composition can be varied, but generally the catalyst composition contains, based on total catalyst composition, at least 0.1% by weight of the oxide or hydroxide of titanium with amounts from about 0.2% by weight to about 50% by weight being preferred and amounts from about 0.2% to about 10% by weight being most preferred.

The oxygen compound of silicon is an inorganic siliceous solid containing a major proportion of silica. In general, suitable inorganic siliceous solids are further characterized by having a relatively large surface area in relation to their mass. The term used herein and one normally used in the art to express the relationship of surface area to mass is "specific surface area". Numerically, specific surface area will be expressed as square meters per gram ($m^2/g$). Generally the inorganic siliceous solid has a specific surface area of at least 1 $m^2/g$ and preferably the average specific surface area is from 25 $m^2/g$ to 800 $m^2/g$.

One class of suitable inorganic siliceous solid are synthetic, porous silica consisting of particles of amorphous silica flocculated or linked together so that they form relatively dense, close-packed masses. Representatives of such materials are silica gel and precipitated silica. These silica products are porous, in that they have numerous pores, voids or interstices throughout their structures. The preparation and properties of such porous siliceous solids are described by R. G. Iler, "The Colloid Chemistry of Silica and Silicates", Cornell University Press, New York, 1955, Chap. VI and U.S. Pat. No. 2,657,149 of R. G. Iler, issued Oct. 27, 1953. A variety of silica gels are available commercially. Commercial silica gels consisting of at least 99% silica and having specific surface area of about 25 $m^2/g$ to about 800 $m^2/g$ and pore volume of about 0.3 to 1.3 ml/g are generally suitable.

Another class of suitable inorganic siliceous solids are synthetic, silica powders consisting of particles of amorphous silica flocculated in open-packed, readily disintegrated, looselyknit aggregates. Representatives of silica powders are fumed, pyrogenic silica obtained by the combustion of hydrogen and oxygen with silicon tetrachloride or tetrafluoride. Fumed silicas are produced commercially and are sold by various companies such as by Cabot Corporation as "Cab-O-Sil" and by Degussa as "Aerosil". Fumed silicas suitably employed as catalyst generally consist of at least 99% silica and have surface area of about 50 $m^2/g$ to about 400 $m^2/g$ and particle size of about 0.007 micron to about 0.05 micron.

Another class of inorganic siliceous solids are synthetic inorganic oxide materials containing a major proportion of silica. Such materials are know as refractory oxides and includes silica-alumina, silica-magnesia, silica-zirconia, silica-alumina-boria and silica-alumina-magnesia.

Other suitable inorganic siliceous solids are naturally-occurring crystalline mineral silicates. Exemplary naturally-occurring mineral silicates are asbestos minerals such as serpentine (hydrous magnesium silicate); clay minerals such as hectorite (magnesium lithium silicate), kaolins and bentonites; micaceous minerals such as phlogopite (potassium magnesium aluminum silicate) and vermiculete (a hydrous magnesium silicate).

Synthetic amorphous inorganic siliceous solids are preferred over naturally-occurring crystalline mineral silicates as catalyst precursors. Particularly preferred synthetic inorganic siliceous solids are those consisting essentially of pure silica, e.g., at least 90% silica.

In certain modifications of the process, it is desirable to include within the catalyst lesser amounts of a catalyst promoter in addition to the oxygen compound of silicon and the oxide or hydroxide of titanium. Suitable catalyst promoters are the alkali metals of atomic number from 11 to 55 inclusive, i.e., sodium, potassium, rubidium and cesium and alkaline earth metals of atomic number from 12 to 56 inclusive, i.e., magnesium, calcium, strontium and barium. The form in which the catalyst promoters are employed is preferably the oxide, although compounds which are readily converted to the oxide are also suitably employed as these are typically converted to the oxide as during pretreatment subsequent to the formation of the initially prepared catalyst composition but prior to use.

When present, the optimum amount of catalyst promoter employed depends in part upon the atomic number of the catalyst promoter. Catalyst promoters of high atomic number, e.g., barium, are generally employed in larger amounts than catalyst promoters of low atomic number, e.g., magnesium. However, the use of excessive amounts of catalyst promoter may be detrimental to catalyst selectivity. In most instances, amounts of catalyst promoters up to about 5% by weight, calculated as metal on total composition, are satisfactory. Amounts of catalyst promoters of up to about 2% by weight are preferred and amounts up to about 0.5% by weight are particularly preferred.

The use of the catalyst promoter, is preferred when employing inorganic silicious solids containing strongly acidic sites, e.g., inorganic siliceous solids having an intrinsic acidity of less than about −3. The intrinsic acidity of an inorganic siliceous solid, generally represented by the term $pK_2$, is determined by titration of an inorganic siliceous solid with an appropriate base in the presence of dye indicators, as disclosed, for example, in U.S. Pat. No. 2,868,688 of Benesi et al., issued Jan. 13, 1959.

The preparation of the catalyst is effected by a variety of techniques. In one technique, the catalyst composition is suitably prepared by calcining a mixture of an inorganic siliceous solid and titanium dioxide at elevated temperatures, e.g., 500° C. to 1000° C. In another technique, the catalyst composition is prepared by co-gelling a mixture of a titanium salt and a silica sol by conventional methods of preparing metal supported catalyst compositions. In still another technique, the catalyst composition is prepared by the surface reaction of silanol groups of an inorganic siliceous solid with a titanium salt by the procedure disclosed in U.S. Pat. No. 3,166,542 of Orzechowski and McKenzie, issued Jan. 19, 1965, U.S. Pat. No. 3,220,959 of Orzechowski, issued Nov. 30, 1965 or U.S. Pat. No. 3,274,120 of Aftandilian, issued Sept. 20, 1966. The catalyst composition is also suitably prepared by the reaction of hydroxyl groups of titanium dioxide containing such groups with a silicon tetrahalide using the same surface reaction procedure disclosed in the above patents. In yet another technique, a catalyst composition comprising a fumed, pyrogenic titania-silica is prepared by the combustion of hydrogen and oxygen with a mixture of silicon tetrahalide and titanium halide in accordance with conventional methods of preparing finely-divided fumed metal oxides and silica. Other techniques for incorporating an oxide or hydroxide of titanium on an inorganic siliceous-solid such as dry-mixing, co-precipitation, impregnation and ion-exchange are also suitably employed.

The catalyst composition in optionally, and preferably, subject to a pretreatment or activation prior to utilization in the process. The precise method of pretreatment will depend in part upon the form of chemical combination in which the components are provided, but in general the pretreatment comprises heating an initially prepared catalyst in an atmosphere of a non-reducing gas such as nitrogen, argon, carbon monoxide or oxygen-containing gas, e.g., air. One function served by this type of pretreatment operation is to convert the catalyst and catalyst promoter components into the form of hydroxides and oxides if these components are not initially provided in these forms. For example, initial catalyst components such as titanium chloride, tetrakismethylpropylaminotitanium and potassium chloride are converted to the corresponding oxide by heating in a non-reducing atmosphere. The pretreatment temperature is not critical and temperatures from about 350° C. to about 800° C. are satisfactory. Typical pretreatment times are from about 1 to 18 hours. Subsequent to pretreatment, the titanium catalyst is employed in any convenient physical form, for example, as powder, flakes, spheres or pellets.

The catalyst composition may suitably incorporate non-interfering substances, especially those that are inert to the reactants and products. Of course, other substances that are known to catalyze the epoxidation of olefinically unsaturated compounds may also be present so long as they do not interfere with the catalytic activity of the titania/silica catalytic combination. Generally, the titania-silica combination may incorporate trace or minor amounts of the oxides or hydroxides of elements such as boron, tin, niobium, tantalum, chromium, molybdenum, tungsten, uranium, bismuth and rare earth elements having atomic number from 57 to 71 inclusive.

THE ALKENE REACTANTS

Suitable alkene reactants have from 3 to 40 carbon atoms, preferably from 3 to 20 carbon atoms and include alkenes such as propylene, isobutylene, hexene-3, decene-1, dodecene-1, triacontene-8, octadecene-1 and tetracontene-1.

Preferred alkene reactants are linear alkenes of from 3 to 40 carbon atoms and particularly preferred alkene reactants are linear, terminal alkenes, i.e., linear alpha-olefins, of from 3 to 20 carbon atoms, especially propylene.

The Hydrocarbon Hydroperoxide

The hydroperoxide reactants of the process of the invention are tertiary alkyl hydroperoxides, i.e., an alkane having a hydroperoxy group substituted on a tertiary carbon atom, or aralkyl hydroperoxides wherein the hydroperoxy group is on a carbon atom attached directly to the aromatic ring. Suitable tertiary alkyl hydroperoxides have from 4 to 20 carbon atoms and include tertiary butyl hydroperoxide, tertiary amyl hydroperoxide, tertiary hexyl hydroperoxide and tertiary octyl hydroperoxide. Suitable aralkyl hydroperoxides have from 7 to 20 carbon atoms and include primary aralkyl hydroperoxides such as benzyl hydroperoxide, secondary aralkyl hydroperoxides such as alphamethylbenzyl hydroperoxide (ethylbenzene hydroperoxide), alpha-ethylbenzyl hydroperoxide and tetralin hydroperoxide and tertiary aralkyl hydroperoxides such as alpha,alpha-dimethylbenzyl hydroperoxide, alpha,alpha-diethylbenzyl hydroperoxide and diisopropylbenzene hydroperoxide. Preferred hydroperoxides are tertiary butyl hydroperoxide and ethylbenzene hydroperoxide.

In the epoxidation reaction, the molar ratio of alkene reactant to hydroperoxide can vary over a wide range and a molar excess of either the alkene reactant or hydroperoxide of up to as high as 100:1 can be used. In general, molar ratios of alkene reactant to hydroperoxide varying from about 50:1 to about 1:10 are satisfactory, although it is preferred to employ molar ratios of alkene reactant to hydroperoxide of about 20:1 to about 1:1.

The hydroperoxide reactant may be supplied in dilute or concentrated, purified or unpurified form. Hydrocarbon hydroperoxides are economically prepared by direct oxidation as exemplified by U.S. Pat. No. 2,845,461 of Winkler et al and U.S. Pat. No. 2,867,666 of Erickson et al. In such oxidations molecular oxygen is passed through hydrocarbon to convert at least a portion of the hydrocarbon to hydroperoxide. Generally, the hydroperoxide is present in concentration of about 5 to 70% by weight in the starting hydrocarbon. Side products such as alcohols and other impurities are also often present in minor amount. This oxidation product may be suitable used without treatment although it may in some cases be preferable to concentrate or purify the hydroperoxide such as by distillation.

The Reaction Conditions

The process of the invention is conducted in the liquid phase in solvents or diluents which are liquid at reaction temperature and pressure and are substantially inert to the reactants and the products produced therefrom. Illustrative suitable solvents are oxygen-containing solvents such as fully esterified polyacyl esters of polyhydroxyalkenes, e.g., glycerol triacetate, tetraccyl esters of erythritol, diethylene glycol diacetate; monoesters such as butyl propionate and phenyl acetate; ketones such as acetone; diethyl ketone and methyl isobutyl ketone, others such as dibutyl ether, dioxane and tetrahydrofuran; as well as nitrogen-containing solvents such as nitriles, e.g., acetonitrile and propionitrile and dialkylamides such as dimethylformamide. Preferred solvents are mononuclear aromatics such as benzene, toluene, chlorobenzene, o-dichlorobenzene; and alkanes such as octane, decane, and dodecane. Particularly preferred solvents are the hydrocarbons employed for producing hydroperoxide reactant, e.g., alkylbenzenes such as ethylbenzene and isopropylbenzene and tertiary alkanes (an alkane containing a carbon atom attached to 3 other carbon atoms) such as isobutane and isohexane. In certain modifications of the epoxidation process, a portion of the olefinic reactant serves as the reaction solvent and not added solvent is needed. In most instances, however, added solvent is used and amounts up to about 20 moles of solvent per mole of organic hydroperoxide are satsifactory. The process is preferably conducted in an inert reaction environment so that the presence of reactive materials such as water is desirably avoided. Suitable reaction conditions are therefore substantially anhydrous.

The epoxidation reaction is suitably conducted by any of a variety of procedures. In one modification, the entire amounts of reactants, the catalyst and the solvent are charged to an autoclave or similar pressure reactor and the reaction mixture is maintained with agitation at reaction temperature and pressure for the desired reaction period. In another modification, one reactant is added to the remaining reaction mixture components in increments, as by adding the hydroperoxide to a mixture of the alkene reactant, the catalyst and the solvent maintained at reaction temperatures and pressure. In yet another modification, reaction is effected in a continuous manner as by contacting the alkene reactant, the hydroperoxide and the solvent during passage through a reaction zone in which the solid catalyst is maintained in particulate form. By any modification, the epoxidation process is conducted at moderate temperatures and pressures. Suitable reaction temperatures vary from about 25° C. to about 200° C., but preferably from 50° C. to 150° C. The reaction is conducted at or above atmospheric pressure. The precise pressure is not critical so long as the reaction mixture is maintained substantially in a non-gaseous phase. Typical pressures vary from about 1 atmosphere to about 100 atmospheres.

At the conclusion of the reaction, the product mixture is separated and the products are recovered by conventional methods such as fractional distillation, selective extraction, filtration and the like. The reaction solvent, the catalyst and any unreacted alkene or hydroperoxide are recycled for further utilization.

The Products

According to the process of the invention the alkene reactant is epoxidized to the corresponding alkene oxide. By way of illustration, propylene oxide is produced from propylene and 1,2-epoxyoctadecane is produced from octadecene-1.

The olefin oxide products are materials of established utility and many are chemicals of commerce. For example, illustrative olefin oxides which are readily prepared by the process of the invention such as propylene oxide, 1,2-epoxybutane, 1,2-epoxydodecane and 1,2-epoxyhexadecane are formulated into useful polymers by polymerization or copolymerization as disclosed by U.S. Pat. Nos. 2,815,343, 2,871,219 and 2,987,489. Propylene oxide is currently prepared commercially by the classic chlorohydrin process and by the reaction of propylene and an organic hydroperoxide in the presence of soluble molybdenum-containing catalyst.

According to the process of the invention the hydrocarbon hydroperoxide is converted to the corresponding alcohol. The alcohol can be recovered as a co-product of the process or reconverted to the hydroperoxide by procedures such as dehydration to olefin, hydrogenation of the olefin and oxidation to hydroperoxide, or by hydrogenolysis to hydrocarbon followed by oxidation to hydroperoxide.

EXAMPLE I

A. A mixture of 25 g of pyrogenic silica having a surface area of 390 m$^2$/g (Cabot Corporation Grade EH-5 Cab-O-Sil) and 1700 ml of n-heptane was dried by heating at reflux in a glass reactor equipped with a Dean Stark trap (to collect water-heptane azeotrope) for a period of 19 hours. After cooling to about 25° C., a 0.47 g (2.5 mmoles) sample of titanium tetrachloride was added to the reactor, and the reaction mixture heated to 97° C. until about 2.5 moles (one equivalent based on TiCl$_4$) of hydrogen chloride had evolved. The evolved HCl was removed by a stream of dry nitrogen and passed into a scrubber containing dilute caustic. About 10 ml of water was than added in 0.5 ml portions to initiate the evolution of additional hydrogen chloride. After a reaction time of about 16 hours at 97° C. the evolution of hydrogen chloride stopped. The reaction mixture was evaporated under reduced pressure at elevated temperature, and the silica residue dried at 120° C./180 mm overnight. The resulting silica product contained 0.4% by weight of titanium, calculated as the metal.

A 1 g sample of the titania-silica composition was contacted with 36.5 g of 1-octene and 4.5 g t-butyl hydroperoxide in 100 ml glass reactor. The reaction conditions, the hydroperoxide conversion and the 1-octene oxide selectivity based on converted hydroperoxide are provided in Table 1 as Run A.

B. A mixture of 25 g of pyrogenic titania having a surface area of about 50 m$^2$/g and a particle size of 15–40 mμ (Degussa Inc. grade P-25 titanium dioxide) and 1700 ml of n-heptane was refluxed in a glass reactor equipped with a Dean Stark trap (to collect water-heptane azeotrope) for a period of 19 hours and then allowed to cool to room temperature. A 7.84 g (0.046 mole) sample of silicon tetrachloride in 25 ml of dry n-heptane was added to the reactor, and the reaction mixture heated at 97° C. until about 0.046 mole of hydrogen chloride had evolved. The evolved hydrogen chloride was removed from the glass reactor into a scrubber of dilute caustic. About 10 ml of water was then added in 0.5 portions to initiate evolution of additional hydrogen chloride. After a reaction time of about 20 hours at 97° C. the evolution of hydrogen chloride again stopped. The reaction mixture was evaporated at about 100° C. under reduced pressure, and the titania residue dried at 120° C./180 mm for 16 hours. The resulting titania product contained 3.2 by weight of silicon, calculated as elemental silicon.

By a procedure similar to that of Example IA, a 1 g sample of the silicon-titania composition was contacted with 36.5 g of 1-octene and 4.5 g of t-butylhydroperoxide. The reaction conditions and results are provided in Table 1 as Run B.

C. A mixture of 3 g pyrogenic silica (Cabot Corporation grade EH-5 Cab-O-Sil) and 1 g of pyrogenic titania (Degussa Inc. grade P-25 titanium dioxide) was intimately mixed and then heated in a furnace at 700° C. for 24 hours. The resulting titania-silica product was powdered by grinding.

By a procedure similar to that of Example IA, a 1 g sample of the titania-silica product was contacted with 36.5 g of 1-octene and 4.5 g of t-butylhydroperoxide. The reaction conditions and results are provided in Table I as Run C.

D. For comparison, a 1 g sample of the pyrogenic titania (Degussa Inc. grade P-25 titanium dioxide) employed for preparing the catalyst compositions of Example IB and IC was contacted with 36.5 g of 1-octene and 4.5 g of t-butylhydroperoxide by a procedure similar to that of Example IA. The reaction conditions and results are provided in Table I and Run D.

E. For comparison, a 1 g sample of the pyrogenic silica (Cabot Corporation EH-5 Cab-O-Sil) employed for preparing the catalyst compositions of Example IA and IC was contacted with 36.5 g of 1-octene and 4.5 g of t-butylhydroperoxide by a procedure similar to that of Example IA. The reaction conditions and results are provided in Table I as Run E.

F. For comparison, a physical mixture of 0.75 g of pyrogenic silica (EH-5 Cab-O-Sil) and 0.25 g of pyrogenic titania (Degussa, P-25) was contacted with 36.5 g of 1-octene and 4.5 g of t-butylhydroperoxide by a procedure similar to that of Example IA. The reaction conditions and results are provided in Table I as Run F.

TABLE I

| Run | Catalyst | Reaction Time, Hr. | Temp ° C. | Hydroperoxide Conversion % | Epoxide Selectivity % |
|---|---|---|---|---|---|
| A | Ti on SiO$_2$ | 4 | 107 | 82.3 | 97.3 |
| B | Si on TiO$_2$ | 21 | 109 | 33.1 | 81 |
| C | TiO$_2$.SiO$_2$ | 10 | 110 | 85 | 91 |
| D | TiO$_2$ | 18 | 110 | 90 | 0 |
| E | SiO$_2$ | 20 | 110 | 37.8 | 10.3 |
| F | TiO$_2$.SiO$_2$ (Physical mixture) | 24 | 110 | 39 | 0 |

EXAMPLE II

A. A solution of 32.86 g of silicon tetrachloride (Matheson, Coleman and Bell semi-conductor grade) and 27.96 g of titanium tetrachloride was added dropwise to 550 ml of deionized water at temperature of about 25° C.–40° C. The resulting mixture was evaporated on a steam bath under reduced pressure and the titania-silica residue dried at a temperature of 150° C. overnight. The titania-silica product contained 48.6% by weight of titanium.

A 1 g sample of the titania-silica product was contacted with 36.5 g of 1-octene, 4.5 g of t-butylhydroperoxide and 2.1 g of nonane diluent in a 100 ml glass reactor. The reaction conditions and results are provided in Table II as Run A.

B. By a procedure similar to that of Example IIA, a titania-silica composition containing 3.9% by weight of titanium was prepared by contacting a solution of 25 ml of silicon tetrachloride and 2.8 g of titanium tetrachloride with 500 ml of deionized water and subsequently recovering the titania-silica product.

A 1 g sample of the titania-silica product was contacted with 36.5 g of 1-octene, 4.5 g of t-butylhydroperoxide and 2.1 g of nonane by a procedure similar to that of Example IIA. The reaction conditions and results are provided in Table II as Run B.

C. By a procedure similar to that of Example IIA, a titania-silica composition containing 1.9% by weight of titanium was prepared by contacting a solution of 36.5 g of silicon tetrachloride and 0.82 g of titanium tetrachloride with 500 ml of deionized water and subsequently recovering the titania-silica product.

A 1 g sample of the titania-silica product was contacted with 36.5 g of 1-octene, 4.5 g of t-butylhydroperoxide and 2.1 g of nonane by a procedure similar to that of Example IIA. The reaction conditions and results are provided in Table II as Run C.

D. By a procedure similar to that of Example IIA, a titania-silica composition containing 0.3% by weight of titanium was prepared by contacting a solution of 36.5 g of silicon tetrachloride and 0.08 g of titanium tetrachloride with 500 ml of deionized water and subsequently recovering the titania-silica product.

A 1 g sample of the titania-silica product was contacted with 36.5 g of 1-octene, 4.5 g of t-butylhydroperoxide and 2.1 g of nonane by a procedure similar to that of Example IIA. The reaction conditions and results are provided in Table II as Run D.

E. A 43 g sample of titanium tetrachloride was added dropwise to 500 ml of deionized water over a period of 15 minutes. The resulting mixture was evaporated on a steam bath and the titania residue was dried at a temperature of 120° C. under reduced pressure (180 mm of Hg) for 20 hours.

For comparison, a 1 g sample of the titania product was contacted with 36.5 g of 1-octene, 4.5 g of t-butylhydroperoxide and 2.1 g of nonane by a procedure similar to that of Example IIA. The reaction conditions and results are provided in Table II as Run E.

F. A 25 ml sample of silicon tetrachloride (Matheson, Coleman and Bell, semi-conductor grade) was added dropwise over a period of 20 minutes to 500 ml of deionized water. The resulting mixture was evaporated on a steam bath under reduced pressure and the silica residue dried at a temperature of 120°/180 mm overnight. Analysis showed that the silica product contained less than 35 ppm of titanium.

A 1 g sample of the silica product was contacted with 36.5 g of 1-octene and 4.5 g of t-butylhydroperoxide in 2.1 g of nonane by a procedure similar to that of Example IIA. The reaction conditions and results are provided in Table II as Run F.

TABLE II

| Run | Catalyst | Catalyst, % W Ti | Temp., °C. | Reaction Time, Hr. | Hydroperoxide Conversion | Epoxide Selectivity |
|---|---|---|---|---|---|---|
| A | $TiO_2.SiO_2$ | 48.6 | 111 | 4.5 | 61 | 84 |
| B | $TiO_2.SiO_2$ | 3.9 | 106 | 2.5 | 73.8 | 92.2 |
| C | $TiO_2.SiO_2$ | 1.9 | 105 | 3 | 75 | 87.2 |
| D | $TiO_2.SiO_2$ | 0.3 | 103 | 5 | 61.3 | 88 |
| E | $TiO_2$ | 60 | 113 | 21 | 73.1 | 9.2 |
| F | $SiO_2$ | 0 | 107 | 20 | 35 | 27 |

EXAMPLE III

A. A mixture of 25 g of commercial pyrogenic silica having a surface area of 390 m²/g (Cabot Corporation grade EH-5 Cab-O-Sil) and 1700 ml of n-heptane was dried by heating at reflux in a glass reactor equipped with a Dean Stark trap (to collect water-heptane azeotrope) for a period of 19 hours. After cooling to about 25° C. a 3.62 g (0.023 mole) sample of titanium trichloride was added to the reactor, and the reaction mixture heated to 97° C. until about 0.023 mole of hydrogen chloride was evolved (one equivalent based in TiCl₃). The hydrogen chloride evolved was removed by a stream of dry nitrogen and passed into a scrubber containing dilute caustic. About 10 ml of water was then added in 0.5 ml portions to initiate the evolution of additional hydrogen chloride. After a reaction time of about 16 hours at 97° C. the evolution of additional hydrogen chloride stopped. The reaction mixture was evaporated under reduced pressure at elevated temperature, and the silica residue dried at 120°/180 mm. The resulting silica product contained 4.2% by weight of titanium.

A 1 g sample of the titania-silica product was contacted with 36.5 g of 1-octene, 4.5 g of t-butylhydroperoxide and 2.1 g of nonane in a 100 ml glass reactor. The reaction conditions and results are provided in Table III as Run A. Subsequent to the completion of the reaction, the titania-silica catalyst was removed from the reaction mixture by filtration. Colorimetric analysis of the reaction mixture filtrate showed the presence of less than 0.02 parts per million of titanium in solution.

B. By a procedure similar to that of Example IIA a titania-silica composition containing 4% by weight of titanium was prepared by contacting 4.68 g of titanium tetrachloride with 25 g of azeotropically dried commercial pyrogenic silica (Cabot Corporation EH-5 Cab-O-Sil) in heptane until one equivalent of HCl (based on $TiCl_4$ charged) was evolved, hydrolyzing the mixture with excess water, and subsequently recovering and drying the titanium-silica product.

A 1 g sample of the titania-silica product was contacted with 36.5 g of 1-octene, 4.5 g of t-butylhydroperoxide and 2.1 g of nonane by a procedure similar to that of Example IIIA. The reaction conditions and results are provided in Table III as Run B. Subsequent to the completion of the reaction, the titanium-silica catalyst was removed from the reaction mixture of filtration. Colorimetric analysis of the reaction mixture filtrate showed the presence of less than 0.4 parts per million of titanium in solution.

C. By a procedure similar to that of Example IIIA a titanium-clay composition containing 4.4% by weight of titanium was prepared by contacting 4.68 g of titanium tetrachloride with 25 g of azeotropically dried Higlo 50 clay (marketed by Georgia Kaolin) in heptane until one equivalent of HCl (based on $TiCl_4$ charged) was evolved, hydrolyzing the mixture with water, and subsequently recovering and drying the titanium-clay product.

A 1 g sample of the titanium-clay product was contacted with 36.5 g of 1-octene, 4.5 g of t-butylhydroperoxide and 2.1 g of nonane by a procedure similar to that of Example IIIA. The reaction conditions and results are provided in Table III as Run C.

TABLE III

| Run | Catalyst | Temp., °C. | Reaction Time, Hr. | Hydroperoxide Conversion | Epoxide Selectivity |
|---|---|---|---|---|---|
| A | $Ti/SiO_2$ | 106 | 2.25 | 64.7 | 93.8 |

TABLE III-continued

| Run | Catalyst | Temp., °C. | Reaction Time, Hr. | Hydroperoxide Conversion | Epoxide Selectivity |
|---|---|---|---|---|---|
| B | Ti/SiO$_2$ | 107 | 1 | 86 | 90 |
| C | Ti/Clay | 103 | 3 | 78 | 77 |
| D | Ti/MgO.SiO$_2$ | 110 | 3 | 72.3 | 87.5 |
| E | Ti/Zr/SiO$_2$ | 106 | 0.5 | 77 | 91 |
| F | Ti/Nb/SiO$_2$ | 110 | 0.5 | 69 | 86 |
| G | Ti/B/SiO$_2$ | 105 | 17 | 99 | 79 |
| H | Ti/Sn/SiO$_2$ | 106 | 4.5 | 75 | 85 |

D. By a procedure similar to that of Example IIIA a titania-magnesia-silica composition containing 3.7% by weight of titanium was prepared by contacting 4.6 g of titanium tetrachloride with 25 g of magnesium silicate gel(10.2 wt. Mg and 35.6% wt. Si; magnesia-silicate marketed by the Floridin Co.) in heptane until one equivalent of hydrogen chloride (based on TiCl$_4$ charged) was evolved, hydrolyzing the mixture with water, and subsequently recovering and drying the titanium-magnesia-silica product.

A 1 g sample of the titania-magnesia-silica product was contacted with 36.5 of 1-octene, 4.5 g of t-butylhydroperoxide and 2.1 of nonane by a procedure similar to that of Example IIIA. The reaction conditions and results are provided in Table III Run D.

E. By a procedure similar to that of Example IIIA a titania-zirconia-silica composition containing 2.9% by weight titanium and 0.5% by weight zirconium was prepared by contacting 1.3 g of zirconium tetrachloride with 25 g of azeotropically dried commercial pyrogenic silica in heptane at 97° C. until one equivalent of HCl (based on ZrCl$_4$ charged) was evolved, charging 1.7 g of titanium tetrachloride and heating at 97° C. until one equivalent of HCl (based on TiCl$_4$ charged) was evolved, hydrolyzing the mixture with water, and subsequently recovering and drying the titania-zirconia-silica product.

A 1 g sample of the titania-zirconia-silica product was contacted with 36.2 g of 1-octene, 4.5 g of t-butylhydroperoxide and 2.1 g of nonane by a procedure similar to that of Example IIIA. The reaction conditions and results are provided in Table III as Run E.

F. By a procedure similar to that of Example IIIA a titania-niobium oxide-silica composition containing 3.3% by weight of titanium and 0.4% by weight of niobium was prepared by contacting 1.4 g of NbCl$_5$ with 25 g of azeotropically dried pyrogenic silica in heptane until one equivalent of HCl (based on bCL$_5$ charged) was evolved, then adding 1.7 g of TiCl$_4$ and contacting at 50° C. until one equivalent of HCl (based on TiCl$_4$ charged) was evolved, hydrolyzing the mixture with water, and subsequently recovering and drying the titania-niobium oxide-silica product.

A 1 g sample of the titania-niobium oxide-silica product was contacted with 36.2 g of 1-octene, 4.5 g of t-butylhydroperoxide and 2.1 g of nonane by a procedure similar to that of Example IIIA. The reaction conditions and results are provided in Table III as Run F.

G. By a procedure similar to that of Example IIIA, E and F a titania-boria-silica composition containing 1.6% by weight of titanium and 0.2% by weight of boron was prepared by the reaction of pyrogenic silica (25 g) with boron trichloride (3.4 g) and then with titanium tetrachloride (2.4 g). The resulting composition was employed as catalyst for the epoxidation of 1-octene by a procedure identical to that of Example IIIA. The reaction conditions and results are provided in Table III as Run G.

H. By a procedure similar to that of Example IIIA, E, and F a titania-tin oxide-silica composition containing 2.4% by weight of titanium and 1.1% by weight of tin was prepared by the reaction of pyrogenic silica (25 g) with titanium tetrachloride (2.4 g) and then with stannic tetrachloride (0.45 g). The resulting composition was employed for the epoxidation of 1-octene by a procedure similar to that of Example IIIA. The reaction conditions and results are provided in Table III as Run H.

EXAMPLE IV

A. A 20 g sample of commercial silica gel having a surface area of 340 m$^2$/g and a pore volume of 1.15 cc/g (Davison grade 62 silica gel preheated at 500° for 2 hours) was contacted with a solution of 2 ml of titanium tetrachloride in 26 ml of 1.72 N hydrochloride acid at a temperature of 25° C. The impregnated silica gel was predried on a steam bath and then contacted with 15 ml of 8 N nitric acid at a temperature of 25° C. The resulting mixture was evaporated on a steam bath, dried at a temperature of 150° C. for 3 hours and then calcined at a temperature of 800° C. for 2 hours. The resulting titania-silica gel composition contained 4.4% by weight of titanium.

A 0.5 g sample of the titania-silica product was contacted with 42 g of 1-octene and 5.5 g of t-butylhydroperoxide in a 100 ml glass reactor. The reaction conditions and results are provided in Table IV as Run A.

B. A 20 g sample of commercial silica gel having a surface area of 340 m$^2$/g and a pore volume of 1.15 cc/g was contacted with a solution of 1 ml of titanium tetrachloride in 24 ml of 1.72 N hydrochloric acid and about 1 ml of 50% wt hydrogen peroxide. The impregnated silica gel was dried on a steam bath at a temperature of 150° C. and then calcined at a temperature of 500° C. for 2 hours. The resulting titania-silica product contained 2.2% by weight of titanium.

A 0.5 g sample of the titania-silica product was contacted with 42 g of 1-octene and 5.5 g of t-butylhydroperoxide by a procedure similar to that of Example IVA. The reaction conditions and results are provided in Table IV as Run B.

C. A 20 g sample of commercial magnesium silicate gel (10.2% wt Mg and 35.6% wt Si; magnesia-silica marketed by the Floridin Co.) having a pore volume of 1.1 cc/g was contacted with a solution of 1 ml of titanium tetrachloride, 4 ml 16 N nitric acid, 1 ml of 50% wt hydrogen peroxide and 10 ml of water. The impregnated magnesium silicate gel was dried at 150° C. and then added calcined at 500° C. for 2 hours. The resulting titania-magnesium silicate composition contained 2.8% by weight of titanium.

A 1 g sample of the titania-magnesia-silica composition was contacted with 42 g of 1-octene and 5.5 g of t-butylhydroperoxide by a procedure similar to that of Example IVA. The reaction conditions and results are provided in Table IV as Run C.

D. A 20 g sample of commercial silica gel having a surface area of 340 m$^2$/g and a pore volume of 1.15 cc/g was contacted with solution of 2 ml titanium tetrachloride, 2.63 g of didymium nitrate (a mixture of La, Nd, Pr and Sm nitrates), 26 ml of 1.72 N hydrochloric acid and 5 ml of 50% wt hydrogen peroxide. The resulting mixture was evaporated on a steam bath, dried at a temperature of 150° C. and then calcined at a temperature of 500° C. for 2 hours. The titania-didymium oxide-silica product contained 4.4% by weight titanium and 4.3% by weight of didymium.

A 0.5 g sample of the titania-didymium oxide-silica product was contacted with 30 g of 1-octene, 4 g of t-butylhydroperoxide and 16 g of n-hexane by a procedure similar to that of Example IVA. The reaction conditions and results are provided in Table IV as Run D.

E. A 20 g sample of commercial silica gel having a surface area of 340 m$^2$/g and a pore volume of 1.15 cc/g was contacted within a solution of 1.73 g of titanium tetrachloride, 0.441 g of ammonium paramolybdate [$(NH_4)_6Mo_7O_{24}.4H_2O$], 20 ml of 9 N nitric acid and 4 ml of 50%w hydrogen peroxide. The impregnated silica gel was dried at 150° C. and then calcined at 500° C. for 2 hours. The resulting silica gel composition contained 2.2% by weight of titanium and 1.2% by weight of molybdenum.

A 1 g sample of the silica gel composition was contacted with 36.5 g of 1-octene and 4.5 g of t-butylhydroperoxide by a procedure similar to that of Example IVA. The reaction conditions and results are provided in Table IV as Run E.

F. A 20 g sample of commercial silica gel having a surface area of 340 m$^2$/g and a pore volume of 1.15 cc/g was contacted with a solution of 1.73 g of titanium tetrachloride, 0.883 g of ammonium paramolybdate [$(NH_4)_6Mo_7O_{24}.4H_2O$], 1.75 g of didymium nitrate (a mixture of rare earth nitrates), 20 ml of 4 N nitric acid and 4 ml of 50%w hydrogen peroxide. The impregnated silica gel was dried at 150° C. and then calcined at 500° C. for 2 hours. The resulting silica gel composition contained 2.2% by weight titanium, 2.4% by weight of molybdenum and 2.9% by weight of rare earth metals.

A 1 g sample of the silica gel composition was contacted with 36.5 g of 1-octene and 4.5 g of t-butylhydroperoxide by a procedure similar to that of Example IVA. The reaction conditions and results are provided in Table IV as Run F.

TABLE IV

| Run | Catalyst | Reaction Time, Hr. | Temp., °C. | Hydroperoxide Conversion % | Epoxide Selectivity % |
|---|---|---|---|---|---|
| A | 4.4% w Ti on SiO$_2$ | 1 | 107 | 56.5 | 91.2 |
| B | 2.2% w Ti on SiO$_2$ | 1 | 107 | 62.2 | 86 |
| C | 2.8% w Ti on MgO.SiO$_2$ | 4 | 110 | 40 | 83.4 |
| D | 4.4% w Ti on SiO$_2$ (4.3% w didymium) | 1 | 88 | 11 | 91.6 |
| E | 2.2% w Ti on SiO$_2$ (1.2% w Mo) | 1 | 105 | 90 | 83 |
| F | 2.2% w Ti on SiO$_2$ (2.4% w Mo, 2.9% w didymium) | ¾ | 104 | 89 | 83 |

EXAMPLE V

Octene-1 and isobutylene were epoxidized with a titania-silica catalyst in glass reactor under the reactions conditions tabulated in Table V. The titania-silica catalyst employed was a pyrogenic silica containing 0.3% by weight of titanium (produced by the flame hydrolysis of SiCl$_4$ and TiCl$_4$).

EXAMPLE VI

A. A 60 g sample of commercial silica gel having a surface area of 340 m$^2$/g and a pore volume of 1.15 cc/g (Davison grade 59 silica) was contacted with a solution of 5.18 g of titanium tetrachloride in 68 ml of 4 N nitric acid and 4 ml of 50% wt hydrogen peroxide. The impregnated silica gel was dried at a temperature of 100° C. and then calcined at a temperature of 800° C. for 2 hours. Analysis of the resulting titania-silica product showed 2.18% by weight of titanium.

TABLE V

| Run | Olefin | Olefin, g | Catalyst, g | Hydroperoxide g | Diluent | Temp., °C. | Reaction Time, Hr. | Hydroperoxide Conversion, % | Epoxide Selectivity, % |
|---|---|---|---|---|---|---|---|---|---|
| 1 | 1-Octene | 52.5 | 1 | Ethylbenzene (3.1g) | Ethylbenzene (18g) | 110 | 17 | 99 | 82 |
| 2 | 1-Octene | 36.5 | 1 | Cumene (7g) | Cumene (1g) | 110 | 20 | 84.3 | 72.3 |
| 3 | 1-Octene | 73 | 2 | t-Butyl (9g) | Nonane (2.1g) | 110 | 3 | 76.8 | 99 |
| 4 | Isobutylene | 6 | 1 | t-Butyl (4.5g) | o-Dichlorobenzene (20 ml) | 112 | 1 | 44.8 | 86.8 |

B. The epoxidation of propylene with ethylbenzene hydroperoxide was conducted in 0.5 inch diameter, 6 feet long fixed bed tubular reactor packed with the titania-silica catalyst of Example VI A. A reaction mixture consisting of 6 moles of propylene per mole of ethylbenzene hydroperoxide in ethylbenzene was continuously fed to the reactor maintained at the indicated temperature and a pressure of 600 psig for a residence time of about 24 minutes. The reaction conditions and the analysis of the product mixture after the indicated reaction time are provided in Table VI.

TABLE VI

| Cumulative Hours | Temp. °C. | Hydroperoxide Conversion, % | Propylene Oxide Selectivity, % |
|---|---|---|---|
| 44 | 100 | 76.8 | 84.0 |
| 83 | 110 | 89.0 | 85.0 |
| 310 | 110 | 85.2 | 83.0 |
| 379 | 114 | 87.6 | 86.5 |

EXAMPLE VII

Titanium as well as several other metals was supported on silica-free supports and the resulting supported metal compositions were tested as catalysts for the epoxidation of 1-octene with t-butyl hydroperoxide (TBHP). The reaction conditions and results are provided in Table VII. In runs A-G the catalyst compositions were prepared by the surface reaction of a metal halide with a pyrogenic alumina having a surface area of 100 m$^2$/g, a Mg(OH) Cl support having a surface area of about 20 m$^2$/g, or a zirconia having a surface area of 169 m²/g by a procedure similar to that of Examples IA and IIIA. In run H a commercial 2.5%w Co-9.5%w Mo on alumina composition marketed by American Cyanamid was employed. In run I, for comparison, the epoxidation of 1-octene with t-butylhydroperoxide was conducted in the absence of a catalyst. and 5 ml of 50% wt hydrogen peroxide, drying the impregnated silica at 150° C. and then calcining at 800° C. for 2 hours. In Run M, the rhenium oxide-silica composition (6.9% wt Re) was prepared by contacting 10 g of commercial pyrogenic silica with 1 g of rhenic acid (HReO₄) in 30 ml of water and subsequently drying the product at 200° C.

TABLE VII

| Run | Catalyst Precursors | Catalyst, Metal on Support | Catalyst, g | Octene-1, g | TBHP, g | Nonane Diluent, g | Temp., °C. | Reaction Time, Hr. | Hydroperoxide Conversion | Epoxide Selectivity % |
|---|---|---|---|---|---|---|---|---|---|---|
| A | TiCl₄(1g), Al₂O₃(25g) | 1.2% Ti | 1 | 36.5 | 9.5 | 2.1 | 110 | 23 | 69 | 13 |
| B | TiCl₄(5g), Al₂O₃(25g) | 4.4% Ti | 1 | 36.5 | 4.5 | 2.1 | 110 | 23 | 74 | 13 |
| C | TiCl₄(4.7g), ZrO₂(25g) | 3.5% Ti | 1 | 36.5 | 4.5 | 2.1 | 111 | 5 | 24 | 18 |
| D | TiCl₄(2.3g), Mg(OH)Cl(12.7g) | 2.9% Ti | 1 | 36.5 | 4.5 | 2.1 | 110 | 4.5 | 60.2 | 6 |
| E | NbCl₅(3.8g), Al₂O₃(25g) | 5% Nb | 1 | 36.5 | 4.5 | 0 | 110 | 22 | 55 | 7 |
| F | TaCl₅(5g), Al₂O₃(25g) | 5% Ta | 1 | 36.5 | 4.5 | 0 | 110 | 23 | 63 | 0 |
| G | ZrCl₄(2.9g), Al₂O₃(25g) | 2.5% Zr | 1 | 36.5 | 4.5 | 2.1 | 110 | 11 | 45 | 1 |
| H | 2.5% w Co-9.5% w Mo on Al₂O₃ | — | 1 | 42 | 5.5 | 0 | 110 | 2 | 70.2 | 21 |
| I | None | — | 0 | 36.5 | 4.5 | 2.1 | 110 | 20 | 17 | 13 |

TABLE VIII

| Run | Catalyst Precursors | Catalyst, % wt Metal | Catalyst, g | Octene-1, g | TBHP, g | Nonane Diluent, g | Temp., °C. | Reaction Time, Hr. | Hydroperoxide Conversion | Epoxide Selectivity % |
|---|---|---|---|---|---|---|---|---|---|---|
| A | WCl₆(2.3g), SiO₂(25g) | 3.8% W | 1 | 36.5 | 4.5 | 2.1 | 105 | 18 | 38.6 | 25.2 |
| B | NbCl₅(3.8g), SiO₂(25g) | 5% Nb | 1 | 36.5 | 4.5 | 2.1 | 108 | 13 | 60 | 1 |
| C | TaCl₅(3g), SiO₂(25g) | 5% Ta | 1 | 36.5 | 4.5 | 2.1 | 110 | 6½ | 40 | 32 |
| D | NbCl₅(0.9g), SiCl₄(36.7g) | 1.4% Nb | 1 | 36.5 | 4.5 | 2.1 | 110 | 7 | 50 | 5 |
| E | NbCl₅(0.08g), SiCl₄(36.7g) | 0.2% Nb | 1 | 36.5 | 4.5 | 2.1 | 103 | 21 | 39.7 | 19.8 |
| F | WCl₆(0.65g), SiCl₄(36.9g) | 1.5% W | 1 | 36.5 | 4.5 | 2.1 | 110 | 70 | 29 | 10 |
| G | WCl₆(0.07g), SiCl₄(36.7g) | 0.3% W | 1 | 36.5 | 4.5 | 2.1 | 110 | 70 | 34 | 14 |
| H | TaCl₅(0.6g), SiCl₄(36.7g) | 3.1% Ta | 1 | 36.5 | 4.5 | 2.1 | 108 | 20 | 53.6 | 7 |
| I | TaCl₅(0.06g), SiCl₄(36.6g) | 0.26% Ta | 1 | 36.5 | 4.5 | 2.1 | 111 | 20 | 45.4 | 14.4 |
| J | CrO₃, SiO₂ | 1.3% Cr | 1 | 35 | 7.5 | 0 | 110 | 1 | 76 | 15 |
| K | CrO₃, MgO.SiO₂ | 0.5% Cr | 1 | 42 | 4.5 | 0 | 110 | 4 | 39 | 18 |
| L | H₂WO₄, SiO₂ | 2.9% W | 1 | 42 | 5.5 | 0 | 110 | 4 | 26.2 | 37.2 |
| M | HReO₄, SiO₂ | 6.9% Re | 1 | 36.5 | 4.5 | 0 | 105 | 1 | 100 | 0 |

EXAMPLE VIII

A variety of metal-silica compositions was prepared and tested as catalysts for the epoxidation of 1-octene with t-butylhydroperoxide (TBHP). The epoxidation reaction conditions and results are provided in Table VIII. In Runs A-C the catalyst compositions were prepared by the surface reaction of a metal halide with a commercial pyrogenic silica (Cabot Corporation EH-5 Cab-O-Sil) by a procedure similar to that of Examples IA and IIIA. In Runs D-I, the catalyst compositions were prepared by the cohydrolysis of a metal halide and silicon tetrachloride by a procedure similar to that of Example II. In Run J, the catalyst composition was prepared by contacting a 50 g sample of commercial silica gel having a surface area of 750 m²/g with a solution of 0.625 g chromium trioxide in 20 ml of water, drying the impregnated silica gel at 150° C. and then calcining at 500° C. for 2 hours. In Run K, the catalyst composition was prepared by contacting a 20 g sample of commercial magnesium silicate gel (10.2%w Mg and 35.6%w Si) having a pore volume of about 1.1 cc/g with a solution of 0.1 g chromium trioxide in 25 ml of water, drying the impregnated magnesium silicate gel at 150° C. and then calcining at 500° C. overnight. In Run L, the catalyst composition was prepared by contacting a 10 g sample of commercial pyrogenic silica having a surface area of 200 m²/g (Cabot Corporation grade MS/7 Cab-O-Sil) with a solution of 0.308 g tungstic acid (H₂WO₄), 45 ml of 25% wt ammonium hydroxide

EXAMPLE IX

In a series of experiments a variety of metal compounds was tested as heterogeneous catalysts for the epoxidation of 1-octene with t-butylhydroperoxide (TBHP). In each experiment a 1 g sample of the indicated metal compound was contacted with 36.5-42 g of 1-octene and 4.5-5.5 g of t-butylhydroperoxide. The reaction conditions and results are provided in Table IX.

EXAMPLE X

A. A 210 g sample of commercial silica-alumina having a pKa of -5, a surface area of 300 m²/g and a pore volume of 0.75 cc/g (Chemetron Chemicals; 97.6% SiO₂ and 1.2% Al₂O₃) was contacted with a solution of 10 ml of titanium tetrachloride, 144 ml of 4 N nitric acid and 18 ml of 50% wt. hydrogen peroxide. The impregnated silica-alumina was dried at 150° C. and then calcined at 800° C. for 2 hours. The resulting silica composition contained 2.2% by weight titanium.

A 1 g sample of the silica-alumina product was contacted with 17 g of 1-octene, 25 g of ethylbenzene hydroperoxide (14.2% wt. in ethylbenzene) and 8 g of nonane in a 100 ml glass reactor at 125° C. for 1.5 hours. The results are provided in Table X as Run A.

B. A 20 g sample of the commercial silica-alumina employed in Example X A was contacted with a solution of 1 ml titanium tetrachloride, 2.31 g of magnesium nitrate hexahydrate, 19 ml of 4H nitric acid and 1 ml of hydrogenperoxide. The impregnated silica-alumina was dried at 160° C. and then calcined at 800° C. for 2 hours. The resulting silica-alumina composition contained 2.2% by weight of titanium and 1.1% by weight of magnesium and had a pKa of 3.3.

The resulting silica-alumina product was employed as catalyst for the epoxidation of 1-octene by a procedure identical to that of Example X A. The results are provided in Table X as Run B.

EXAMPLE XI

A series of experiments were conducted in which propylene was reacted with ethylbenzene hydroperoxide in the presence of a variety of catalysts in a 300 ml stainless steel autoclave. The catalyst, the amount of reactants, the epoxidation reaction conditions, the conversion of hydroperoxide and the selectivity to propylene oxide based on converted hydroperoxide are provided in Table XI. The $Ti/SiO_2$ catalyst employed in Run 1 was prepared by a procedure similar to that described in Example I.

TABLE IX

| Run Catalyst | Nonane Diluent, g | Reaction Time, Hr. | Temp., °C. | Hydroperoxide Conversion, % | Epoxide Selectivity, % |
|---|---|---|---|---|---|
| $TiO_2$ (Cabot Corp.) | 2.1 | 20 | 110 | 50 | 0 |
| $TiO_2$ (Degussa, Inc.) | 2.1 | 18 | 110 | 40 | 0 |
| $TiO_2$ (hydrolyzed $TiCl_4$) of Example II E | 2.1 | 21 | 113 | 73.1 | 9.2 |
| $Bi_2Ti_2O_7$ | 0 | 4 | 110 | 48 | 6 |
| $MgTiO_3$ | 2.1 | 12 | 116 | 28 | 1 |
| $SrTiO_3$ | 2.1 | 16 | 111 | 35 | 1 |
| $CaTiO_3$ | 2.1 | 16 | 110 | 28 | 1 |
| $ZrO_2$ | 2.1 | 20 | 107 | 76.7 | 1 |
| $(NH_4)_4ZrF_6$ | 0 | 2 | 110 | 24 | 5 |
| $ZrB_2$ | 0 | 2 | 110 | 85 | 0 |
| $CaZrO_3$ | 0 | 2 | 110 | 10 | 0 |
| $Nb_2O_5$ | 0 | 4.5 | 115 | 9 | 0 |
| $Ta_2O_5$ | 0 | 4.5 | 110 | 11 | 5 |
| $CrO_3$ | 0 | 0.5 | 108 | 99 | 22 |
| $CrCl_3$ | 0 | 1.5 | 96 | 98 | 0 |
| WC | 2.1 | 112 | 116 | 56 | 5 |
| $WO_3$ | 0 | 22 | 111 | 85 | 8 |
| $Re_2O_7$ | 0 | 4 | 110 | 100 | 0 |
| $TeO_2$ | 0 | 22 | 110 | 33 | 7 |
| $SeO_2$ | 0 | 3 | 110 | 97 | 0 |
| $UO_2$ | 0 | 20 | 110 | 55 | 5 |

C. A 20 g sample of the commercial silica-alumina employed in Example X A was contacted with a solu-

TABLE XI

| RUN | CATALYST (4.75 g) | PROPYLENE | ETHYLBENZENE HYDROPEROXIDE | ETHYLBENZENE | REACTION TIME | TEMP. °C. | HYDROPEROXIDE CONVERSION | EPOXIDE SELECTIVITY |
|---|---|---|---|---|---|---|---|---|
| 1 | ~4% Ti on Silica (Cabot Corp. EH-5 Cab-O-Sil) | 35 g. | 33.2 g. | 61.7 g. | 4 hr. | 110–112 | 86% | 41% |
| 2 | Silica (Cabot Corp. EH-5 Cab-O-Sil) | 38 g | 32.9 g. | 61.3 g. | 4 hr. | 110–115 | 30.5% | 12% |
| 3 | Titania (Degussa P-25) | 36 g. | 33.1 g. | 61.5 g. | 4 hr. | 110–111 | 53% | 2.4% | tion of 1 ml of titanium tetrachloride, 2.12 g of calcium nitrate tetrahydrate, 19 ml of 4 N nitric acid and 1 ml of 50% wt. hydrogen peroxide. The impregnated silica-alumina was dried at 160° C. and then calcined at 800° C. for 2 hours. The resulting silica-alumina product contained 2.2% by weight of titanium and 1.8% by weight of calcium and had a pKa of 1.5.

The silica-alumina product was employed as catalyst for the epoxidation of 1-octene by a procedure idential to that of Example X A. The results are provided in Table X as Run C.

TABLE X

| Run | Catalyst | Hydroperoxide Conversion, % | Epoxide Selectivity % |
|---|---|---|---|
| A | 2.2% w Ti on $SiO_2.Al_2O_3$ | 74.1 | 29.1 |
| B | 2.2% w Ti/1.1% w Mg on $SiO_2.Al_2O_3$ | 80.9 | 72.7 |
| C | 2.2% w Ti/1.8% w Ca on $SiO_2.Al_2O_3$ | 93.3 | 66.3 |

EXAMPLE XII

A variety of alkali metal or alkaline earth metal promoted titania/silica catalyst compositions were prepared. Each catalyst composition was prepared by dissolving 4 g of titanium tetrachloride and a calculated amount of an alkali metal or alkaline earth salt (2.0 g $Ca(NO_3)_2$, 1.5 g or 3.0 g $Mg(NO_3)_2$, 0.95 g or 1.9 g $NaNO_3$, 1.55 g or 3.1 g KI) in 100 ml of absolute methanol. The resulting solution was poured over 100 g of silica gel having a surface area of 340 m$^2$/g and a pore volume of 1.15 cc/g. The methanol was removed in a rotary evaporator and the resulting impregnated silica gel was calcined for 2 hours at 800° C. The resulting catalyst compositions contained about 1% by weight of titanium, calculated as the metal.

Each of the catalyst compositions prepared above was employed for the epoxidation of 1-octene. Each epoxidation reaction was conducted by contacting 1 g of the indicated catalyst composition, 28.6 g of 12%w ethylbenzene hydroperoxide (in ethylbenzene) and 17 g of 1-octene at 100° C. for 1 hour. The catalyst composition employed, the conversion of hydroperoxide and the selectivity to 1-octene oxide based on converted hydroperoxide are provided in Table XII.

TABLE XII

| Catalyst Compositions | Hydroperoxide Conversion, % | Epoxide Selectivity, % |
|---|---|---|
| 1% w Ti/0.5% w Ca/SiO$_2$ | 86 | 90 |
| 1% w Ti/0.25% w Mg/SiO$_2$ | 67 | 91 |
| 1% w Ti/0.5% w Mg/SiO$_2$ | 58 | 91 |
| 1% w Ti/0.25% w Na/SiO$_2$ | 90 | 89 |
| 1% w Ti/0.5% w Na/SiO$_2$ | 73 | 93 |
| 1% w Ti/0.25% w K/SiO$_2$ | 91 | 87 |
| 1% w Ti/0.25% w K/SiO$_2$ | 90 | 88 |

EXAMPLE XIII

The epoxidation of propylene with ethylbenzene hydroperoxide was conducted with a 1%w Ti/0.5%w Ca on silica gel catalyst prepared by a procedure similar to that described in Example XII. The epoxidation reaction was conducted in a 0.5 inch diameter, 2.5 foot long fixed bed tubular reactor packed with the catalyst. A reaction mixture consisting of 6 moles of propylene per mole of ethylbenzene hydroperoxide in ethylbenzene was continuously fed to the reactor to give a residence time of about 30 minutes. The reactor was maintained at the indicated temperature and a pressure of 600 psig. The reaction conditions and the analyses of the product mixture after the indicated reaction times are provided in Table XIII:

TABLE XIII

| Temp., °C. | Hours on Catalyst | Hydroperoxide Conversion, % | Epoxide Selectivity, % |
|---|---|---|---|
| 90 | 170 | 96.2 | 89.2 |
| 90 | 215 | 94.9 | 91.6 |
| 97 | 400 | 97 | 88 |
| 103 | 500 | 98.0 | 87 |
| 110 | 563 | 99.6 | 86.2 |

We claim as our invention:

1. A process of epoxidizing propylene by reacting, in liquid phase in inert solvent at a temperature of about 25° C. to 200° C., propylene with a hydrocarbon hydroperoxide selected from tertiary alkyl hydroperoxide of from 4 to 20 carbon atoms and aralkyl hydroperoxide of from 7 to 20 carbon atoms wherein the hydroperoxy group is on a carbon atom attached directly to an aromatic ring in the presence of a heterogeneous essentially insoluble catalyst composition comprising an inorganic oxygen compound of silicon in chemical combination with at least 0.1% by weight, based on total catalyst composition, of an oxide or hydroxide of titanium.

2. The process of claim 1 wherein the hydroperoxide is tertiary butyl hydroperoxide and the catalyst composition comprises an inorganic siliceous solid containing at least 90% by weight of silica in chemical combination with about 0.2% to about 50% by weight of the oxide or hydroxide of titanium.

3. The process of claim 1 wherein the hydroperoxide is ethylbenzene hydroperoxide and the catalyst composition comprises an inorganic siliceous solid containing at least 90% by weight of silica in chemical combination with about 0.2% to about 50% by weight of the oxide or hydroxide of titanium.

4. The process of claim 1 wherein the catalyst composition additionally contains up to about 5% by weight, based on the total catalyst composition, of an alkali metal of atomic number from 11 to 55 inclusive or an alkaline earth metal or atomic number from 12 to 56 inclusive.

5. The process of claim 4 wherein the catalyst composition contains from about 0.2% to about 10% by weight of the oxide or hydroxide of titanium, based on total catalyst composition in chemical combination with an inorganic siliceous solid containing at least 90% by weight silica.

6. The process of claim 5 wherein the catalyst composition contains an alkaline earth metal in an amount of up to about 2% by weight of the total catalyst composition.

7. The process of claim 6 wherein the alkaline earth metal is present in an amount of up to about 1% by weight of the total catalyst composition.

8. A process of epoxidizing a linear terminal alkene of 3 to 40 carbon atoms by reacting, in liquid phase an inert solvent at a temperature of about 25° C. to 200° C., the alkene with a hydrocarbon hydroperoxide selected from tertiary alkyl hydroperoxide of from 4 to 20 carbon atoms and aralkyl hydroperoxide of from 7 to 20 carbon atoms wherein the hydroperoxy group is on a carbon atom attached directly to an aromatic ring in the presence of a heterogeneous, essentially insoluble catalyst composition comprising an inorganic oxygen compound of silicon in chemical combination with at least 0.1% by weight, based on total catalyst composition, of an oxide or hydroxide of titanium.

9. The process of claim 8 wherein the catalyst composition additionally contains up to about 5% by weight, based on the total catalyst composition, of an alkali metal of atomic number from 11 to 55 inclusive or an alkaline earth metal of atomic number from 12 to 56 inclusive.

10. The process of claim 9 wherein the catalyst composition contains from about 0.2% to about 10% by weight of the oxide or hydroxide of titanium, based on total catalyst composition in chemical combination with an inorganic siliceous solid containing at least 90% by weight silica.

11. The process of claim 10 wherein the catalyst composition contains an alkaline earth metal in an amount of up to about 2% by weight of the total catalyst composition.

12. The process of claim 8 wherein the catalyst composition comprises an inorganic siliceous solid in chemical combination with about 0.2% to about 50% by weight of an oxide or hydroxide of titanium.

13. The process of claim 12 wherein the inorganic siliceous solid contains at least 90% by weight of silica and the reaction temperature is about 50° C. to about 150° C.

14. The process of claim 13 wherein the inorganic siliceous solid is silica gel.

15. The process of claim 14 wherein the molar ratio of alkene to hydroperoxide is from about 20:1 to 1:1.

16. The process of claim 15 wherein the hydroperoxide is tertiary butyl hydroperoxide.

17. The process of claim 16 wherein the alkene is 1-octene.

18. The process of claim 15 wherein the hydroperoxide is ethylbenzene hydroperoxide.

19. The process of claim 18 wherein the alkene is 1-octene.

* * * * *